(12) United States Patent
Suzuki

(10) Patent No.: US 8,449,570 B2
(45) Date of Patent: May 28, 2013

(54) FORCEPS FOR ENDOSCOPE

(75) Inventor: Keita Suzuki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 27 days.

(21) Appl. No.: 13/335,262

(22) Filed: Dec. 22, 2011

(65) Prior Publication Data

US 2012/0158043 A1    Jun. 21, 2012

Related U.S. Application Data

(63) Continuation of application No. PCT/JP2011/062457, filed on May 31, 2011.

(30) Foreign Application Priority Data

Jun. 28, 2010    (JP) ............................... P2010-146517

(51) Int. Cl.
     *A61B 17/00*      (2006.01)

(52) U.S. Cl.
     USPC ........................................................ 606/205

(58) Field of Classification Search
     USPC .......................... 606/174, 205, 206, 207, 208
     See application file for complete search history.

(56) References Cited

U.S. PATENT DOCUMENTS

| | | | |
|---|---|---|---|
| 3,958,576 A * | 5/1976 | Komiya | 606/142 |
| 5,782,834 A | 7/1998 | Lucey et al. | |
| 5,906,629 A | 5/1999 | Oren et al. | |
| 6,299,630 B1 * | 10/2001 | Yamamoto | 606/205 |
| 6,409,678 B1 * | 6/2002 | Ouchi | 600/562 |
| 7,344,553 B2 * | 3/2008 | Opolski et al. | 606/207 |
| 7,871,422 B2 * | 1/2011 | Shibata | 606/205 |
| 2001/0021860 A1 * | 9/2001 | Ouchi | 606/205 |
| 2002/0143358 A1 * | 10/2002 | Domingo et al. | 606/190 |

(Continued)

FOREIGN PATENT DOCUMENTS

| | | |
|---|---|---|
| DE | 101 37 122 A1 | 2/2003 |
| JP | 2001-321385 A | 11/2001 |

(Continued)

OTHER PUBLICATIONS

European Search Report dated May 21, 2012 from corresponding European Patent Application No. EP 11 80 0559.4.

(Continued)

*Primary Examiner* — Ryan Severson
*Assistant Examiner* — Jonathan W Miles
(74) *Attorney, Agent, or Firm* — Scully, Scott, Murphy & Presser, P.C.

(57) ABSTRACT

A forceps for endoscope includes: a pair of first and second forceps members that is supported by a forceps rotary shaft so as to be relatively rotatable; an opening and closing wire that is moved forward and backward in the direction of the axis so that the first forceps member and the second forceps member are rotated relatively; a stopper that switches an angle in which the first forceps member and the second forceps member rotate relatively at first and second positions different from each other in the direction of the axis; an adjusting wire is moved forward and backward in the direction of the axis; and a sheath through which the opening and closing wire and the adjusting wire are inserted and in which the first forceps member, the second forceps member, and the stopper protrude from the front end thereof.

9 Claims, 7 Drawing Sheets

U.S. PATENT DOCUMENTS

2005/0004432 A1* 1/2005 Suzuki et al. ............... 600/146
2005/0187547 A1 8/2005 Sugi
2009/0112229 A1* 4/2009 Omori et al. ............... 606/130

FOREIGN PATENT DOCUMENTS

| JP | 2003-126103 A | 5/2003 |
|---|---|---|
| JP | 2007-044330 A | 2/2007 |
| JP | 4197983 B2 | 12/2008 |

OTHER PUBLICATIONS

English language abstract only of Japanese Patent Application No. JP 2004-321660 dated Nov. 18, 2004.
International Search Report PCT/JP2011/062457 dated Jul. 5, 2011.

* cited by examiner

FORCEPS FOR ENDOSCOPE

This application is a continuation application whose priority is claimed on Japanese Patent Application No. 2010-146517, filed on Jun. 28, 2010, based on a PCT Patent Application No. PCT/JP2011/062457, filed on May 31, 2011, and the contents of which both the PCT Application and the Japanese Patent Application are incorporated herein by reference.

BACKGROUND OF THE INVENTION

1. Field of the Invention

The present invention relates to a forceps for endoscope which is used while being inserted into a body cavity.

2. Description of the Related Art

Conventionally, a forceps for endoscope (hereinafter, simply referred to as a "treatment instrument") are known that is used to perform various surgical techniques on a tissue inside a body cavity of a patient or the like while being inserted into the body cavity.

As an example of the treatment instrument, there is a known forceps which is disclosed in Japanese Patent No. 4197983. A distal end of the forceps is provided with a pair of forceps members which is supported through a rotary shaft so as to be relatively rotatable.

The pair of forceps members is connected to an operating section on the proximal side by an operating wire which is inserted through an elongated sheath. Two link members are attached to the distal end of the operating wire so as to be rotatable, and the distal ends of the respective link members are respectively attached to one proximal end and the other proximal end of the pair of forceps members so as to be rotatable.

Accordingly, when the operating wire is moved forward and backward in the axial direction through the operating section, the pair of forceps members rotates relatively about the rotary shaft so that the forceps are opened.

SUMMARY OF THE INVENTION

A forceps for endoscope according to a first aspect of the present invention includes: a pair of forceps members that is supported by a rotary shaft so as to be relatively rotatable; an opening and closing operating member configured to be moved forward and backward in the axial direction so that the forceps members rotate relatively by an opened angle in accordance with the movement amount; an adjusting member that switches the maximal movement amount of the opening and closing operating member at a first position and a second position different from each other in the axial direction; and an adjusting wire configured to be moved forward and backward in the axial direction so that the adjusting member moves between the first position and the second position.

In a forceps for endoscope according to a second aspect of the present invention, the adjusting member according to the first aspect is a stopper that regulates the forward and backward movement of the opening and closing operating member.

In a forceps for endoscope according to a third aspect of the present invention, the forceps for endoscope according to the second aspect further includes a locking portion that is formed in the opening and closing operating member and configured to be capable of coming into contact with the stopper, wherein when the locking portion comes into contact with the stopper with the forward and backward movement of the opening and closing operating member, the forward and backward movement of the opening and closing operating member is regulated.

In a forceps for endoscope according to a fourth aspect of the present invention, the adjusting member according to the first aspect is a stopper that regulates the relative rotation of the proximal ends of the pair of forceps members at any one of the first position and the second position.

In a forceps for endoscope according to a fifth aspect of the present invention, in the forceps for endoscope according to the fourth aspect, the distal end of the stopper is provided with a concave portion, and when the proximal ends of the pair of forceps members come into contact with a inner peripheral surface of the concave portion, the relative rotation of the proximal ends of the pair of forceps members is regulated.

In a forceps for endoscope according to a sixth aspect of the present invention, in the forceps for endoscope according to either one of the fourth or fifth aspects, the distal end of the opening and closing operating member is branched into two parts so that the two parts extend in a curved manner so as to face each other, one distal end of the opening and closing operating member is connected to one proximal end of the pair of forceps members, and the other distal end of the opening and closing operating member is connected to the other proximal end of the pair of forceps members.

In a forceps for endoscope according to a seventh aspect of the present invention, the forceps for endoscope according to any one of the first to sixth aspects further includes an operating portion that is provided in each of the proximal ends of the opening and closing operating member and the adjusting wire so as to move the opening and closing operating member and the adjusting wire forward and backward.

In a forceps for endoscope according to an eighth aspect of the present invention, in the forceps for endoscope according to any one of the first to seventh aspects, the first position is a position where the opened angle between the forceps members becomes a maximal opened angle, and the second position is a position where the opened angle between the forceps members becomes half of the maximal opened angle.

In a forceps for endoscope according to a ninth aspect of the present invention, the forceps for endoscope according to any one of the first to eighth aspects further includes a sheath through which the opening and closing operating member and the adjusting wire are inserted and in which the forceps member is positioned at the distal end side thereof, wherein the adjusting member is provided at the distal end side of the sheath.

Figure 1:
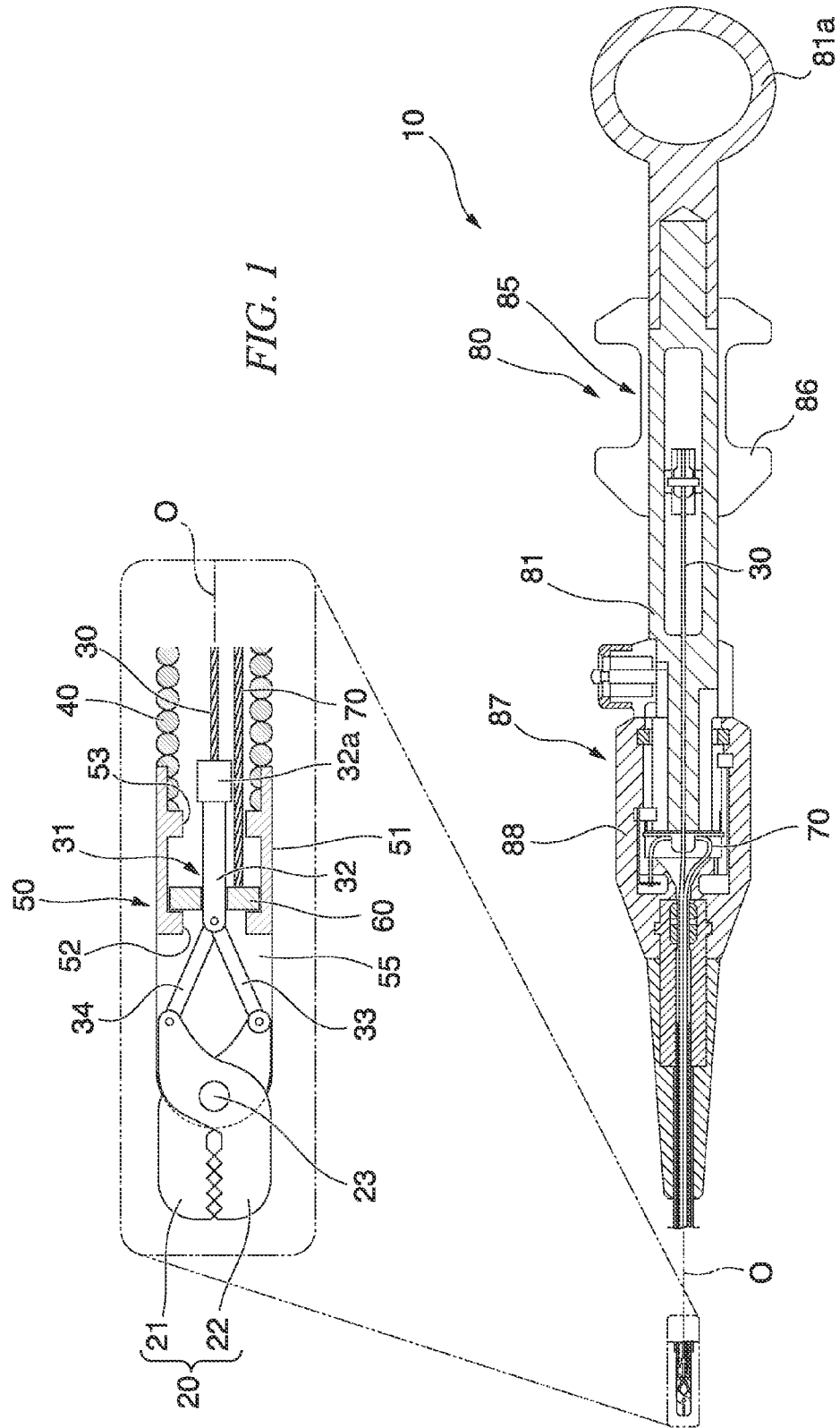
FIG. 1 is a vertical cross-sectional view showing forceps for endoscope according to a first embodiment.

DETAILS DESCRIPTION OF THE INVENTION (First Embodiment)

Hereinafter, a first embodiment of the present invention will be described in detail with reference to FIGS. 1 to 4.

As shown in FIGS. 1 to 4, a forceps for endoscope (hereinafter, simply referred to as a "treatment instrument") 10 of the first embodiment of the present invention includes: a treatment section 20; an opening and closing wire (an opening and closing operating member) 30; a sheath 40; a front cover member 50; a stopper (an adjusting member) 60; an adjusting wire 70; and an operating section 80.

Figure 2:
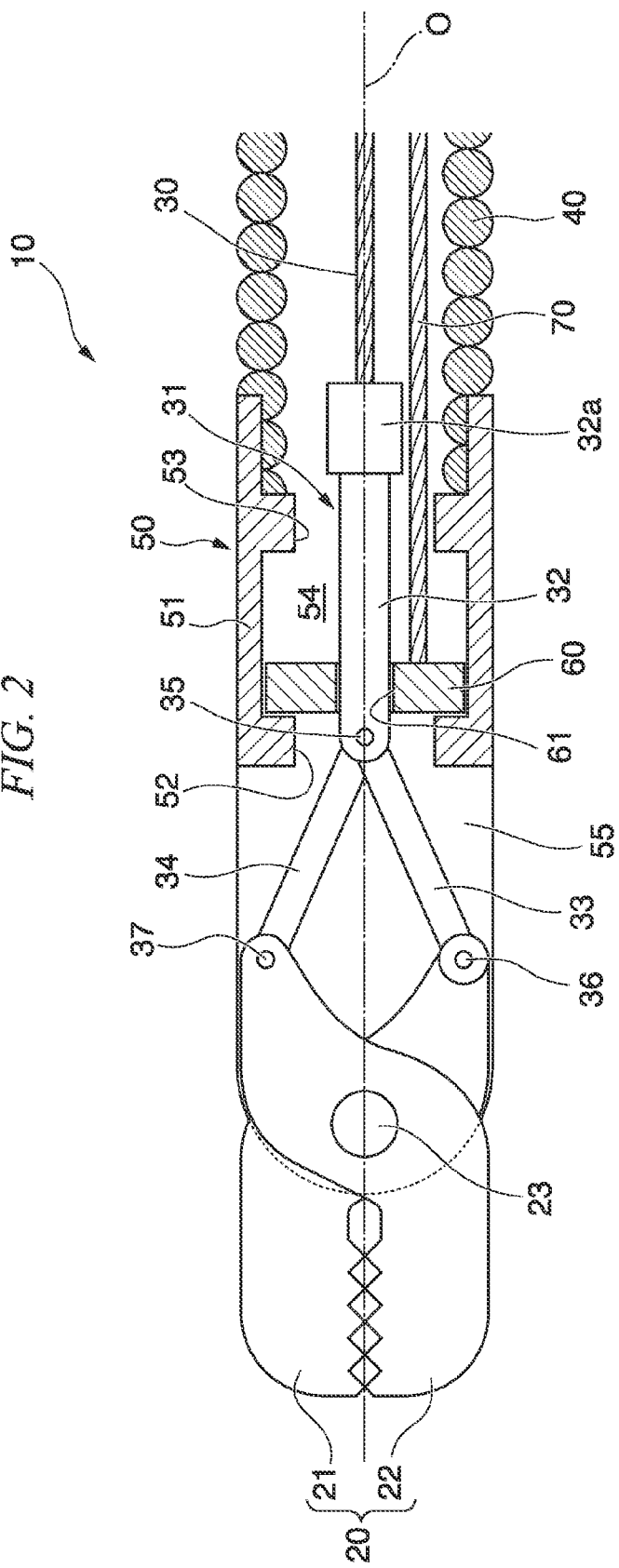
FIG. 2 is a vertical cross-sectional view showing a case where a pair of forceps members of a distal end of the forceps for endoscope according to the first embodiment is fully closed.
Figure 3:
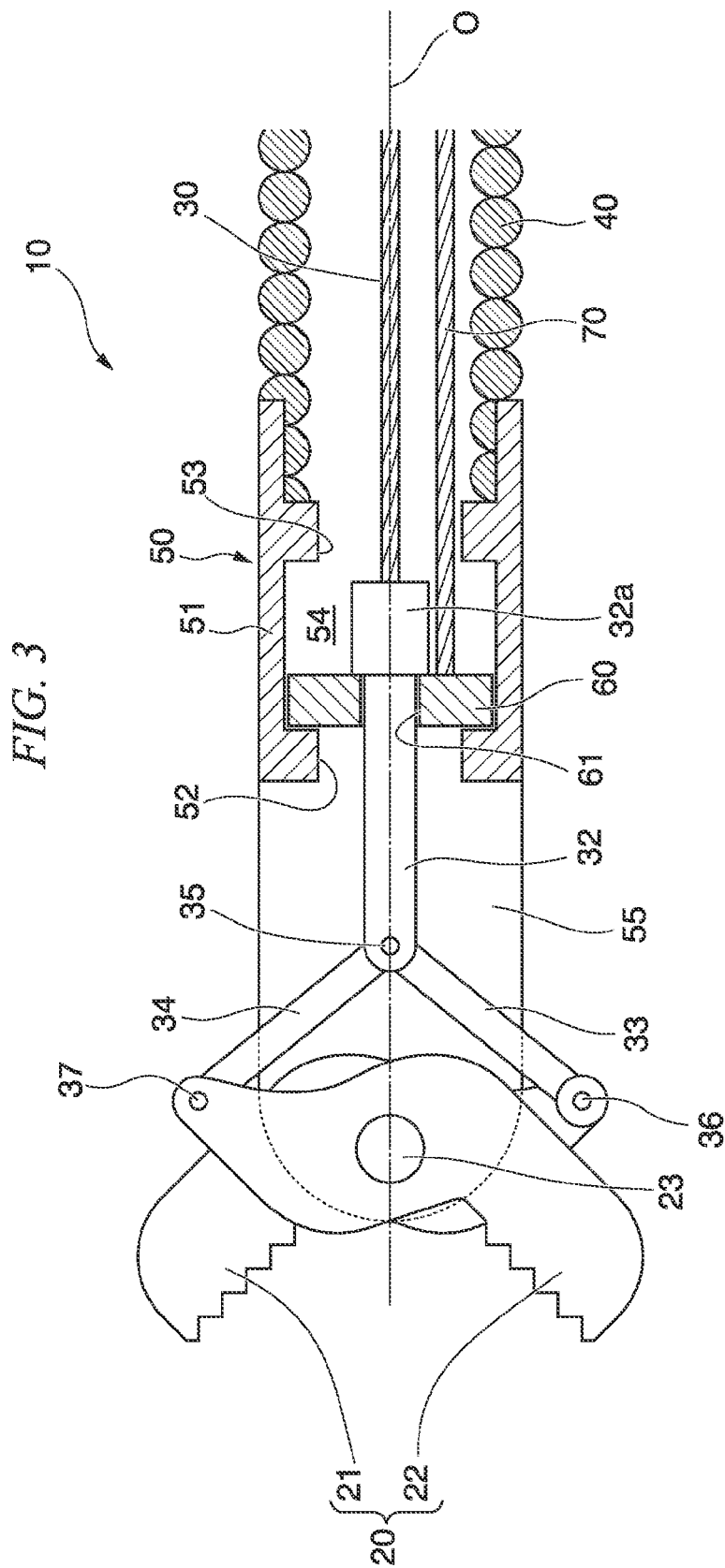
FIG. 3 is a vertical cross-sectional view showing a case where the pair of forceps members of the distal end of the forceps for endoscope according to the first embodiment is fully opened.
Figure 4:
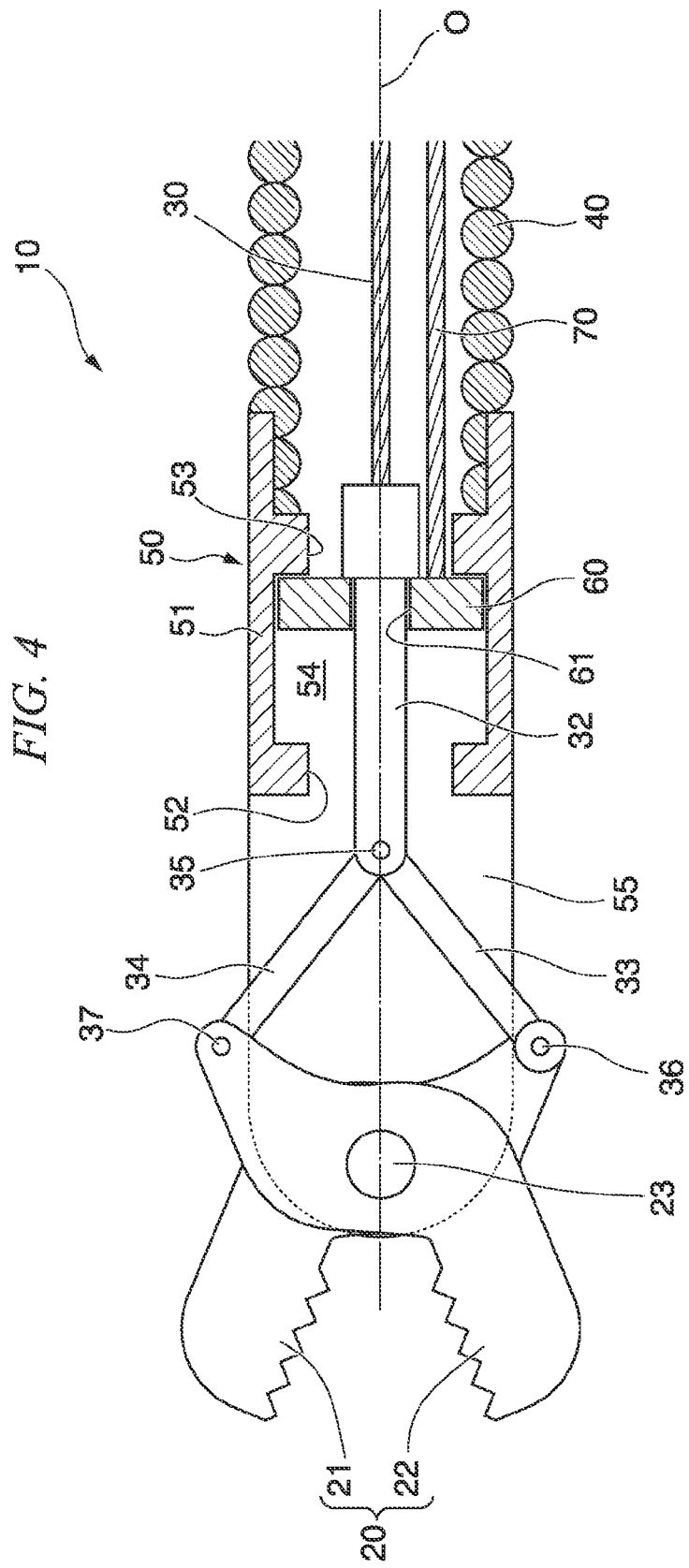
FIG. 4 is a vertical cross-sectional view showing a case where the pair of forceps members of the distal end of the forceps for endoscope according to the first embodiment is half opened.

The treatment section 20 is used to perform a treatment on a tissue inside a body cavity, and as shown in FIGS. 2 to 4, includes a pair of forceps members with a first forceps member 21 and a second forceps member 22.

The first forceps member 21 and the second forceps member 22 are arranged so as to intersect with each other at substantial center of the extension direction thereof, and are connected to each other at the intersecting position through a forceps rotary shaft 23. Accordingly, the first forceps member 21 and the second forceps member 22 are configured to be relatively rotatable about the forceps rotary shaft 23, thereby switching to a closed state where the distal ends of the first forceps member 21 and the second forceps member 22 come into contact with each other and an opened state where the distal ends of the first forceps member 21 and the second forceps member 22 separate from each other. In other words, the first forceps member 21 and the second forceps member 22 are supported by the forceps rotary shaft 23 so as to be capable of being opened and closed. The forceps rotary shaft 23 is supported by a cover 55 which is disposed with the first forceps member 21 and the second forceps member 22 interposed therebetween. The cover 55 is integrally formed with the front cover member 50.

The opening and closing wire 30 extends along the axis O. The opening and closing wire 30 is a flexible wire which is formed of, for example, metal such as stainless steel, and is inserted through the sheath 40. The proximal end of the opening and closing wire 30 is connected to the operating section 80, and the distal end thereof is connected to the proximal end of the treatment section 20 through a link mechanism 31.

The link mechanism 31 is attached to the distal end of the opening and closing wire 30. The link mechanism 31 includes: a pin member 32 which extends along the axis O of the opening and closing wire 30 and is formed in a bar shape and a pair of link members which includes a first link member 33 and a second link member 34. The proximal end of the pin member 32 is provided with a locking portion 32a of which the outer peripheral surface is formed so as to increase in diameter by one level. Further, the first link member 33 and the second link member 34 are respectively connected to the distal end of the pin member 32 through a common rotary shaft 35 which is parallel to the forceps rotary shaft 23. Accordingly, the first link member 33 and the second link member 34 are configured to be respectively rotatable about the common rotary shaft 35.

Furthermore, the distal end of the first link member 33 is connected to the proximal end of the first forceps member 21 through a first link rotary shaft 36 so as to be rotatable. Further, the distal end of the second link member 34 is connected to the proximal end of the second forceps member 22 through a second link rotary shaft 37 so as to be rotatable. The first link rotary shaft 36 and the second link rotary shaft 37 respectively separate from the axis O by substantially the same distance so as to face each other with the axis O of the opening and closing wire 30 interposed therebetween, and are arranged so as to be parallel to the forceps rotary shaft 23 and the common rotary shaft 35.

The sheath 40 is formed by densely wrapping a thin metallic wire in a loop shape about the axis O. Further, the sheath 40 is formed in a coil shape and is flexible. The opening and closing wire 30 and the adjusting wire 70 to be described later are inserted through the inner peripheral side of the coil shape of the sheath 40. The proximal end of the sheath 40 is connected to the operating section 80, and the distal end of the sheath 40 is attached to the front cover member 50.

The front cover member 50 includes: a substantially cylindrical portion 51 which is formed about the axis O and a pair of covers 55 which extends from the outer peripheral portion of the distal end of the cylindrical portion 51 in substantially parallel to the axis O so as to face the cylindrical portion 51 with the axis O interposed therebetween. The front cover member 50 is integrally fixed to the sheath 40 so as to face the cylindrical portion 51 in a manner such that the proximal end of the cylindrical portion 51 is fitted to the outside of the sheath 40.

A first contact portion 52, of which the inner peripheral surface is formed so as to decrease in diameter by one level, is formed at a position of the inner peripheral surface of the cylindrical portion 51 near the distal end. Furthermore, as in the first contact portion 52, a second contact portion 53 of which the inner peripheral surface is formed so as to decrease in diameter by one level is formed at a position of the inner peripheral surface of the cylindrical portion 51 distant toward the proximal end from the first contact portion 52. The space which is formed between the first contact portion 52 and the second contact portion 53 on the inner peripheral side of the cylindrical portion 51 is formed as a stopper accommodating portion 54.

The stopper 60 is a disk-like member, and is disposed inside the stopper accommodating portion 54 while the center axis is aligned with the axis O. The outer diameter of the stopper 60 is set to be approximately equal to or slightly smaller than the inner diameter of the inner peripheral surface of the cylindrical portion 51. Furthermore, the thickness of the stopper 60, that is, the dimension thereof in the direction of the axis O is set to be smaller than the dimension of the stopper accommodating portion 54 in the direction of the axis O, that is, the separation distance between the first contact portion 52 and the second contact portion 53 in the direction of the axis O. Accordingly, the stopper 60 is configured to be movable in the direction of the axis O between the first contact portion 52 and the second contact portion 53 inside the stopper accommodating portion 54.

Hereinafter, the position where the stopper 60 comes into contact with the first contact portion 52 is set as a first position of the stopper 60, and the position where the stopper 60 comes into contact with the second contact portion 53 is set as a second position of the stopper 60. Furthermore, the first position and the second position are positions which are away from each other in the direction of the axis O, and the second position is positioned at the proximal side in the direction of the axis O in relation to the first position.

Further, the stopper 60 is provided with a penetration hole 61 which penetrates the stopper along the axis O. The pin member 32 of the link mechanism 31 is configured to be relatively movable inside the penetration hole 61 in the direction of the axis O. Furthermore, the inner diameter of the penetration hole 61 is set to a dimension in which the locking portion 32a of the pin member 32 is not able to be inserted through the penetration hole. Accordingly, the locking portion 32a of the pin member 32 may come into contact with the proximal end surface of the stopper 60. When the locking portion 32a comes into contact with the stopper 60, the forward and backward movement of the opening and closing wire 30 is regulated.

As in the opening and closing wire 30, the adjusting wire 70 is a flexible wire which is formed of, for example, metal such as stainless steel. The adjusting wire 70 extends substantially parallel to the axis O along the opening and closing wire 30 and is inserted through the sheath 40. The proximal end of the opening and closing wire 30 is connected to the operating section 80, and the distal end of the opening and closing wire 30 is connected to the proximal end surface of the stopper 60. Accordingly, the stopper 60 moves forward and backward with the forward and backward movement of the adjusting wire 70 in the direction of the axis O.

Next, the operating section 80 will be described with reference to FIG. 1. The operating section 80 includes a thin and long operating section body 81 which extends along the axis O. The operating section body 81 is provided with an opening and closing wire operating portion 85 and an adjusting wire operating portion 87. The proximal end of the operating section body 81 is provided with a finger-grip handle 81a which is used so that a finger is hooked thereon. Further, the proximal end of the sheath 40 is connected to the distal end of the operating section body 81.

The opening and closing wire operating portion 85 includes a slider 86 which is provided at a portion on the proximal end side of the operating section body 81 in relation to the center thereof in the direction of the axis O. The slider 86 is able to slide by a predetermined range in the direction of the axis O. Further, the proximal end of the opening and closing wire 30 which is inserted through the operating section body 81 from the distal end of the operating section body 81 is connected to the slider 86. The opening and closing wire 30 is relatively movable inside the operating section body 81 in the direction of the axis O relative to the operating section body 81. Accordingly, the opening and closing wire 30 moves forward and backward in the direction of the axis O with the forward and backward movement of the slider 86 in the direction of the axis O.

The adjusting wire operating portion 87 includes a rotary handle portion 88 which is provided at a portion on the distal end side of the operating section body 81 in relation to the center thereof in the direction of the axis O. The rotary handle portion 88 is fitted to the outside of the operating section body 81 so as to be relatively rotatable about the axis O. Further, the inner peripheral surface of the rotary handle portion 88 is connected with the proximal end of the adjusting wire 70 which is inserted through the operating section body 81 from the distal end of the operating section body 81 and extends while going around the axis O in the circumferential direction inside the rotary handle portion 88. Accordingly, the adjusting wire 70 further goes around the axis O in the circumferential direction or is extracted outward with the rotation of the rotary handle portion 88 about the axis O, whereby the adjusting wire 70 moves forward and backward in the direction of the axis O.

Next, the operation of the treatment instrument 10 with the above-described configuration will be described. In the treatment instrument 10 of the embodiment, the opening and closing wire 30 is connected to the first forceps member 21 and the second forceps member 22 through the link mechanism 31, so that the first forceps member 21 and the second forceps member 22 rotate relatively with the forward and backward moving operation of the opening and closing wire 30 in the direction of the axis O. Then, with the forward and backward movement of the opening and closing wire 30 through such a forward and backward moving operation of the opening and closing wire operating portion 85, the state of the treatment section 20 may be switched to the closed state where the distal ends of the first forceps member 21 and the second forceps member 22 come into contact with each other and the opened state where the distal ends separate from each other.

That is, when the slider 86 of the opening and closing wire operating portion 85 is slid to the proximal end side of the operating section body 81, as shown in FIG. 2, the opening and closing wire 30 is moved backward to the rearmost side in the direction of the axis O. At this time, the proximal ends of the first forceps member 21 and the second forceps member 22 are pulled to the proximal side in the direction of the axis O through the first link member 33 and the second link member 34 of the link mechanism 31, whereby the proximal ends of the first forceps member 21 and the second forceps member 22 approach each other so as to be closest to each other. Accordingly, it becomes the closed state where the distal ends of the first forceps member 21 and the second forceps member 22 come into contact with each other.

On the other hand, when the slider 86 of the opening and closing wire operating portion 85 slides to the distal end side of the operating section body 81, as shown in FIGS. 3 and 4, the opening and closing wire 30 moves forward to the front side in the direction of the axis O. Accordingly, the first link member 33 and the second link member 34 of the link mechanism 31 press the proximal ends of the first forceps member 21 and the second forceps member 22 so as to be widened, so that the proximal ends of the first forceps member 21 and the second forceps member 22 separate from each other about the rotary shaft. In accordance with this movement, it becomes the opened state where the distal ends of the first forceps member 21 and the second forceps member 22 rotate so as to separate from each other.

Then, in the embodiment, when the stopper 60 is displaced to the first position and the second position, the opened state of the first forceps member 21 and the second forceps member 22 in the treatment section 20 may be switched to the full-opened state and the half-opened state.

That is, when the rotary handle portion 88 of the adjusting wire operating portion 87 is rotated, the adjusting wire 70 moves forward to the front side in the direction of the axis O. Accordingly, as shown in FIG. 3, the stopper 60 comes into contact with the first contact portion 52 of the cylindrical portion 51 of the front cover member 50, so that the stopper 60 is disposed at the first position. In this state, when the slider 86 of the opening and closing wire operating portion 85 is slid to the distal end side of the operating section body 81, the opening and closing wire 30 moves forward to the position where the locking portion 32a of the pin member 32 provided in the distal end of the opening and closing wire 30 comes into contact with the stopper 60 of the first position.

Here, in the opened state, the separation distance between the distal ends of the first forceps member 21 and the second forceps member 22, that is, the opened angle between the distal ends of the first forceps member 21 and the second forceps member 22 becomes larger as the opening and closing wire 30 moves forward to the front side in the direction of the axis O. Then, as described above, the state where the locking portion 32a comes into contact with the stopper 60 disposed at the first position corresponds to the state where the opening and closing wire 30 moves forward to the farthest side in the direction of the axis O. At this time, the opened angle between the distal ends of the first forceps member 21 and the second forceps member 22 is fully opened. In this way, when the stopper 60 is positioned at the first position, the first forceps member 21 and the second forceps member 22 may be switched to the full-opened state and the full-closed state in a manner such that the opening and closing wire 30 moves forward and backward.

On the other hand, when the rotary handle portion 88 of the adjusting wire operating portion 87 is rotated reversely, the adjusting wire 70 moves backward to the proximal side in the direction of the axis O. Accordingly, as shown in FIG. 4, the stopper 60 comes into contact with the second contact portion 53 in the cylindrical portion 51 of the front cover member 50, so that the stopper 60 is disposed at the second position. In this state, when the slider 86 of the opening and closing wire operating portion 85 is slid to the distal end side of the operating section body 81, the opening and closing wire 30 moves forward to the position where the locking portion 32a of the pin member 32 provided in the distal end of the opening and closing wire 30 comes into contact with the stopper 60 of the second position.

At this time, since the stopper 60 of the second position is positioned at the proximal side in the direction of the axis O compared to the case of the first position, the opening and closing wire 30 is positioned at the proximal side in the direction of the axis O compared to the case of the full-opened state. Then, as described above, the opened angle between the distal ends of the first forceps member 21 and the second forceps member 22 becomes smaller as the opening and closing wire 30 moves forward to the proximal side in the direction of the axis O. For this reason, the opened angle becomes the half-opened state which is smaller than the case of the full-opened state. In this way, when the stopper 60 is positioned at the second position, the first forceps member 21 and the second forceps member 22 may be switched to the half-opened state and the full-closed state in a manner such that the opening and closing wire 30 moves forward and backward.

With such a configuration, in the treatment instrument 10 of the embodiment, the range of the opened angle between the first forceps member 21 and the second forceps member 22 may be switched depending on the case where the stopper 60 as the adjusting member is positioned at the first position and the second position. That is, since the angle range where the first forceps member 21 and the second forceps member 22 may rotate relatively may be switched, the first forceps member 21 and the second forceps member 22 may be easily changed to the full-opened state, the half-opened state, and the closed state.

Further, the first forceps member 21, the second forceps member 22, and the stopper 60 are respectively arranged so as to protrude from the distal end of the sheath 40, and the angle range where the first forceps member 21 and the second forceps member 22 rotate relatively is switched at the front of the sheath 40. Accordingly, the opened angle between the first forceps member 21 and the second forceps member 22 may be made to be the same in the full-opened state and the half-opened state at all times.

That is, when the treatment is performed by using the treatment instrument 10, the sheath 40 has a curved or loop shape. At this time, for example, when the stopper serving as the adjusting member is disposed at the proximal end side of the sheath 40 so that the forward and backward movement range of the opening and closing wire 30 is regulated by the stopper, the opening and closing wire 30 may not be moved forward and backward by a desired amount due to the influence of the curved or loop shape of the sheath 40 and the full-opened state or the half-opened state may not be made to be the same at all times. However, according to the treatment instrument 10 of the embodiment, as described above, the adjustment is performed at the distal end side of the sheath 40, the full-opened state and the half-opened state may be accurately realized without being influenced by the curved or loop shape of the sheath 40.

From the description above, according to the treatment instrument 10 of the present invention, the forceps members may be easily and accurately half opened.

Furthermore, since the forward and backward movement of the opening and closing wire 30 and the adjusting wire 70 may be easily performed by operating the operating section 80 on the proximal end side, that is, on the hand side of the user, the operability may be improved.

Furthermore, since the locking portion 32a comes into contact with the stopper 60 with the forward and backward movement of the opening and closing wire 30, the forward and backward movement of the opening and closing wire 30 is regulated. Accordingly, the forward and backward movement range of the opening and closing wire 30 changes depending on the case where the stopper 60 is positioned at the first position and the second position. Accordingly, the angle range where the first forceps member 21 and the second forceps member 22 rotate relatively may be easily and reliably switched.

(Second Embodiment)

Next, a second embodiment of the present invention will be described with reference to FIGS. 5 to 7. Furthermore, in the second embodiment, the same reference numerals for the same components as those of the first embodiment will be used a detailed description of the same components will be omitted here.

A treatment instrument 100 of the second embodiment of the present invention includes: a treatment section 120, an opening and closing wire (an opening and closing operating member) 130; the sheath 40; a front cover member 150; a stopper (an adjusting member) 160; the adjusting wire 70; and the operating section 80. Furthermore, the operating section 80 of the second embodiment of the present invention has the same configuration as that of FIG. 1, and when the operating section 80 is operated, the opening and closing wire 130 and the adjusting wire 70 may be moved forward and backward.

Figure 5:
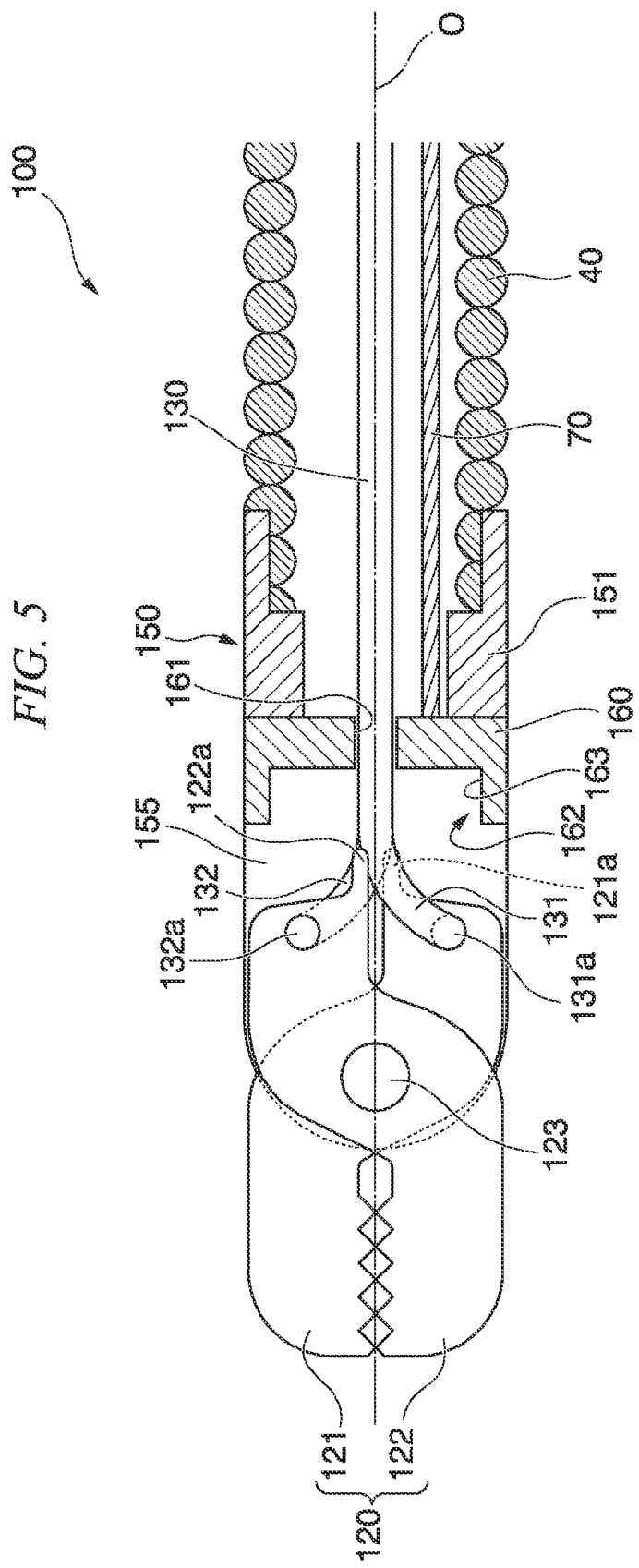
FIG. 5 is a vertical cross-sectional view showing a case where a pair of forceps members of a distal end of forceps for endoscope according to a second embodiment is fully closed.
Figure 6:
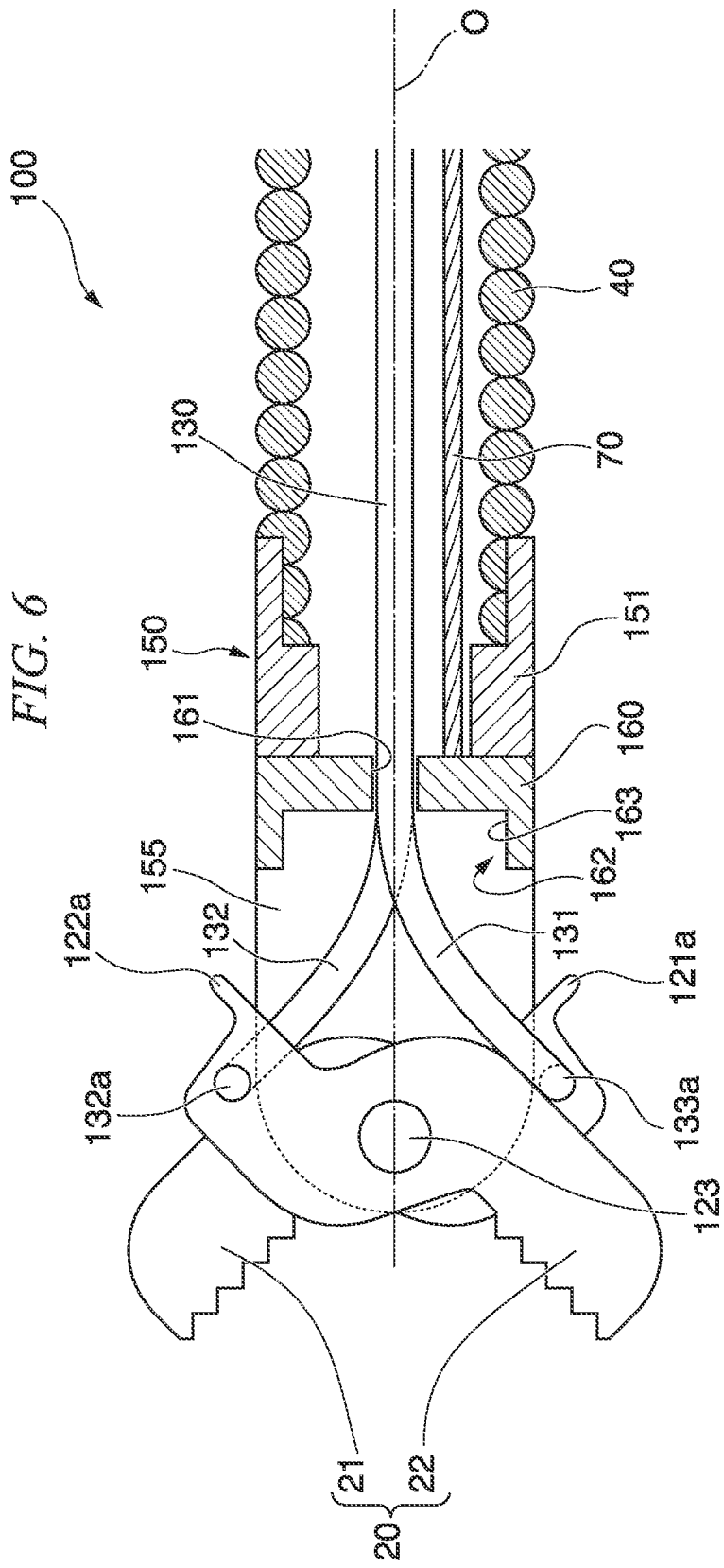
FIG. 6 is a vertical cross-sectional view showing a case where the pair of forceps members of the distal end of the forceps for endoscope according to the second embodiment is fully opened.
Figure 7:
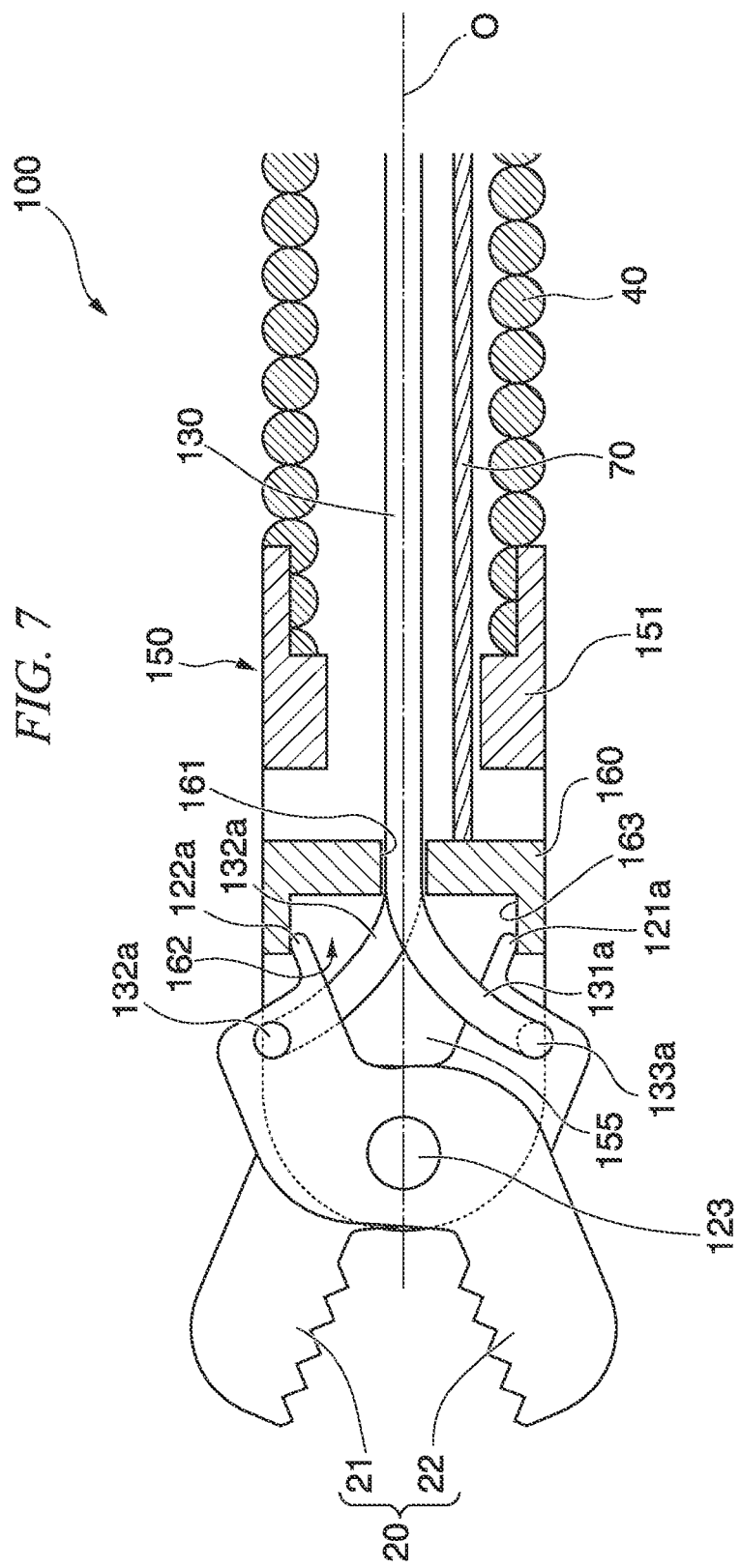
FIG. 7 is a vertical cross-sectional view showing a case where the pair of forceps members of the distal end of the forceps for endoscope according to the second embodiment is half opened.

The treatment section 120 is used to perform a treatment on a tissue inside a body cavity, and as shown in FIGS. 5 to 7, includes a pair of forceps members with a first forceps member 121 and the second forceps member 122. The first forceps member 121 and the second forceps member 122 are arranged so as to intersect with each other at substantial center of the extension direction thereof, and are connected to each other at the intersecting position through a forceps rotary shaft 123. Accordingly, the first forceps member 121 and the second forceps member 122 are configured to be relatively rotatable about the forceps rotary shaft 123.

Further, the first forceps member 121 and the second forceps member 122 of the second embodiment of the present invention are provided with convex portions 121a and 122a which protrude from the proximal ends thereof. Furthermore, the forceps rotary shaft 123 is supported by a cover 155 which is disposed with the first forceps member 121 and the second forceps member 122 interposed therebetween. The cover 155 is integrally formed with the front cover member 150.

The opening and closing wire 130 extends along the axis O. The opening and closing wire 130 is a flexible wire which is formed of, for example, metal such as stainless steel, and is inserted through the sheath 40. The proximal end of the opening and closing wire 130 is connected to the operating section 80, and the distal end thereof is provided with a first wire branched portion 131 and a second wire branched portion 132 which are formed by branching the opening and closing wire 130 into two parts.

The first wire branched portion 131 and the second wire branched portion 132 extend in a curved manner so as to face each other with the axis O interposed therebetween as it moves to the distal end side in the axis O. Then, the distal end of the first wire branched portion 131 is rotatably connected to the proximal end of the first forceps member 121 through the first rotary shaft 131a. Further, the distal end of the second wire branched portion 132 is rotatably connected to the proximal end of the second forceps member 122 through the second rotary shaft 132a. The first rotary shaft 131a and the second rotary shaft 132a respectively separate from the axis O by substantially the same distance so as to face each other with the axis O interposed therebetween, and are arranged in parallel to the forceps rotary shaft 123.

The front cover member 150 includes: a substantially cylindrical portion 151 which is formed about the axis O and a pair of covers 155 which extends from the outer peripheral portion of the distal end of the cylindrical portion 151 in substantially parallel to the axis O so as to face the cylindrical portion 151 with the axis O interposed therebetween. The front cover member 150 is integrally fixed to the sheath 40 in a manner such that the proximal end of the cylindrical portion 151 is fitted to the outside of the sheath 40.

A stopper 160 is disposed at the distal end side of the front cover member 150, and includes a penetration hole 161 which extends along the axis O. Further, the opening and closing wire 130 is inserted through the penetration hole 161. Furthermore, the stopper 160 slidably comes into contact with the pair of covers 155 at both sides in the radial direction of the axis O. Accordingly, the stopper 160 is disposed at the distal end side of the front cover member 150 so as to move forward and backward along the axis O correspond to a direction of the opening and closing wire 130.

The distal end of the stopper 160 is provided with a concave portion 162 which is depressed to the proximal side in the direction of the axis O. In addition, the concave portion 162 is provided with an inner peripheral surface 163 which faces the inside in the radial direction of the axis O. Furthermore, the inner peripheral surface 163 may have a facing surface in at least the facing direction of the first rotary shaft 131 a and the second rotary shaft 132a, that is, the relative rotation direction of the proximal ends of the first forceps member 121 and the second forceps member 122.

Furthermore, the distal end of the adjusting wire 70 is fixed to the proximal end surface of the stopper 160. Accordingly, the stopper 160 moves forward and backward with the forward and backward movement of the adjusting wire 70 in the direction of the axis O. Hereinafter, the position where the stopper 160 comes into contact with the distal end surface of the front cover member 150 is set as the first position of the stopper 160. The position where the stopper 160 is disposed to be away from the distal end surface of the front cover member 150 and the convex portions 121a and 122a of the first forceps member 121 and the second forceps member 122 are accommodated inside the concave portion 162 of the stopper 160 is set as the second position of the stopper 160.

The first position and the second position are positions which are away from each other in the direction of the axis O, and the second position is positioned at the front side in the direction of the axis O in relation to the first position.

Next, the operation of the treatment instrument 100 with the above-described configuration will be described. In the treatment instrument 100 of the second embodiment of the present invention, the distal end of the opening and closing wire 130 is branched into the first wire branched portion 131 and the second wire branched portion 132, the first wire branched portion 131 is connected to the proximal end of the first forceps member 121 through the first rotary shaft 131a, and the second wire branched portion 132 is connected to the proximal end of the second forceps member 122 through the second rotary shaft 132a. Accordingly, when the opening and closing wire 130 is moved forward and backward in the direction of the axis O, the first forceps member 121 and the second forceps member 122 may rotate relatively. Then, when the opening and closing wire 130 moves forward and backward, the state of the treatment section 120 may be switched to a closed state where the distal ends of the first forceps member 121 and the second forceps member 122 come into contact with each other and an opened state where the distal ends thereof separate from each other.

That is, the slider 86 of the opening and closing wire operating portion 85 is slid to the proximal end side of the operating section body 81, as shown in FIG. 5, the opening and closing wire 130 moves to the rearmost side in the direction of the axis O. At this time, the proximal ends of the first forceps member 121 and the second forceps member 122 are pulled into the proximal side in the direction of the axis O by the first wire branched portion 131 and the second wire branched portion 132. Accordingly, the proximal ends of the first forceps member 121 and the second forceps member 122 approach each other so as to be closest each other. Accordingly, it becomes the closed state where the distal ends of the first forceps member 121 and the second forceps member 122 come into contact with each other.

Furthermore, when the first forceps member 121 and the second forceps member 122 are in the closed state, the convex portions 121a and 122a of the first forceps member 121 and the second forceps member 122 are closest to each other, and extend in parallel to the axis O. Then, when the adjusting wire 70 is moved forward so that the stopper 160 moves forward, the convex portions 121a and 122a are accommodated inside the concave portion 162 of the stopper 160.

On the other hand, when the slider 86 of the opening and closing wire operating portion 85 is slid to the distal end side of the operating section body 81, as shown in FIGS. 6 and 7, the opening and closing wire 130 moves forward to the distal side in the direction of the axis O. In this state, the first wire branched portion 131 and the second wire branched portion 132 which extend in a curved manner so as to face each other with the axis O interposed therebetween press the proximal ends of the first forceps member 121 and the second forceps member 122, so that the proximal ends of the first forceps member 121 and the second forceps member 122 separate from each other about the rotary shaft. In accordance with this movement, it becomes the opened state where the distal ends of the first forceps member 121 and the second forceps member 122 rotate so as to separate from each other.

Then, in the embodiment, when the stopper 160 is displaced to the first position and the second position, the opened state of the first forceps member 121 and the second forceps member 122 in the treatment section 120 may be switched to the full-opened state and the half-opened state.

That is, when the rotary handle portion 88 of the adjusting wire operating portion 87 is rotated so that the adjusting wire 70 moves backward to the proximal side in the direction of the axis O, the stopper 160 comes into contact with the distal end surface of the front cover member 150, and the stopper 160 is disposed at the first position. In this state, when the slider 86 of the opening and closing wire operating portion 85 is slid to the distal end side of the operating section body 81, the opening and closing wire 130 moves forward, and the first forceps member 121 and the second forceps member 122 rotate relatively so that the proximal end of the first forceps member 121 and the proximal end of the second forceps member 122 separate from each other by the first wire branched portion 131 and the second wire branched portion 132. At this time, the relative rotation range of the first forceps member 121 and the second forceps member 122 is not regulated, and the first forceps member 121 and the second forceps member 122 rotate relatively in accordance with the movement length of the opening and closing wire 130. As shown in FIG. 6, the first forceps member 121 and the second forceps member 122 are fully opened.

On the other hand, when the rotary handle portion 88 of the adjusting wire operating portion 87 is rotated reversely so that the adjusting wire 70 moves forward to the front side in the direction of the axis O, the stopper 160 separates from the distal end surface of the front cover member 150, so that the convex portions 121*a* and 122*a* of the first forceps member 121 and the second forceps member 122 are accommodated inside the concave portion 162 of the stopper 160. In this state, when the slider 86 of the opening and closing wire operating portion 85 is slid to the distal end side of the operating section body 81, the opening and closing wire 130 moves forward, and the first forceps member 121 and the second forceps member 122 rotate relatively so that the proximal end of the first forceps member 121 and the proximal end of the second forceps member 122 separate from each other by the first wire branched portion 131 and the second wire branched portion 132.

Then, when the first forceps member 121 and the second forceps member 122 rotate relatively, the convex portions 121*a* and 122*a* of the first forceps member 121 and the second forceps member 122 respectively come into contact with the inner peripheral surface 163 of the concave portion 162 of the stopper 160, so that the relative rotatable angle range of the first forceps member 121 and the second forceps member 122 is regulated. Accordingly, as shown in FIG. 7, the opened angle between the first forceps member 121 and the second forceps member 122 becomes the half-opened state which is smaller than the case of the full-opened state.

With such a configuration, even in the treatment instrument 100 of the second embodiment of the present invention, as in the first embodiment, the stopper 160 serving as the adjusting member may switch the relative rotatable angle of the first forceps member 121 and the second forceps member 122 in accordance with the first position and the second position. Accordingly, the first forceps member 121 and the second forceps member 122 may be easily switched to the full-opened state, the half-opened state, and the closed state.

Further, even in the treatment instrument 100, as in the first embodiment, the adjustment is performed at the distal end side of the sheath 40. Accordingly, the full-opened state and the half-opened state may be accurately realized at all times without being influenced by the curved or loop shape of the sheath 40.

Accordingly, according to the treatment instrument 100 of the second embodiment of the present invention, the forceps members may be easily and accurately half opened.

Further, the distal end of the opening and closing wire 130 is branched into the first wire branched portion 131 and the second wire branched portion 132 and extends in a curved manner so as to face each other so that the wire branched portions are connected to the proximal ends of the first forceps member 121 and the second forceps member 122. Accordingly, it is possible to easily rotate the first forceps member 121 and the second forceps member 122 relative to each other by moving the opening and closing wire 130 forward and backward.

Furthermore, the stopper 160 which is movable forward and backward to the first position and the second position is provided, and the proximal ends of the first forceps member 121 and the second forceps member 122 are accommodated inside the concave portion 162 when the stopper 160 is positioned at the second position, thereby easily and reliably switching the relative rotatable angle range of the first forceps member 121 and the second forceps member 122 with the displacement of the stopper 160 between the first position and the second position.

While the treatment instruments 10 and 100 of the embodiments of the present invention have been described, the embodiment of the present invention is not limited thereto, and may be appropriately modified without departing from the technical spirit of the present invention.

For example, in the embodiments, the stoppers 60 and 160 are adopted as the adjusting member, and the relative rotatable angle range of the first forceps members 21 and 121 and the second forceps members 22 and 122 is switched depending on the case where the stoppers 60 and 160 are positioned at the first position and the second position. However, any adjusting member may be used if the relative rotatable angle range of the first forceps members 21 and 121 and the second forceps members 22 and 122 is able to be switched.

The invention claimed is:

1. A forceps for endoscope comprising:
 a pair of forceps members that is supported by a rotary shaft so as to be relatively rotatable;
 an opening and closing operating member configured to be moved forward and backward in an axial direction and rotating the forceps members relatively by an opened angle in accordance with the movement amount;
 an adjusting member that switches a maximal movement amount of the opening and closing operating member at a first position and a second position different from each other in the axial direction; and
 an adjusting wire configured to be moved forward and backward in the axial direction so that the adjusting member moves between the first position and the second position.

2. The forceps for endoscope according to claim 1, wherein the adjusting member is a stopper that regulates the forward and backward movement of the opening and closing operating member.

3. The forceps for endoscope according to claim 2, further comprising:
 a locking portion that is formed in the opening and closing operating member and configured to be capable of coming into contact with the stopper,
 wherein when the locking portion comes into contact with the stopper with the forward and backward movement of the opening and closing operating member, the forward and backward movement of the opening and closing operating member is regulated.

4. The forceps for endoscope according to claim 1, wherein the adjusting member is a stopper that regulates the relative rotation of the proximal ends of the pair of forceps members at any one of the first position and the second position.

5. The forceps for endoscope according to claim 4, wherein the distal end of the stopper is provided with a concave portion, and
   wherein when the proximal ends of the pair of forceps members come into contact with a inner peripheral surface of the concave portion, the relative rotation of the proximal ends of the pair of forceps members is regulated.

6. The forceps for endoscope according to claim 4,
   wherein the distal end of the opening and closing operating member is branched into two parts so that the two parts extend in a curved manner so as to face each other,
   wherein one distal end of the opening and closing operating member is connected to one proximal end of the pair of forceps members, and
   wherein the other distal end of the opening and closing operating member is connected to the other proximal end of the pair of forceps members.

7. The forceps for endoscope according to claim 1, further comprising:
   an operating portion that is provided in each of the proximal ends of the opening and closing operating member and the adjusting wire so as to move the opening and closing operating member and the adjusting wire forward and backward.

8. The forceps for endoscope according to claim 1,
   wherein the first position is a position where the opened angle between the forceps members becomes a maximal opened angle, and
   wherein the second position is a position where the opened angle between the forceps members becomes a half of the maximal opened angle.

9. The forceps for endoscope according to claim 1, further comprising:
   a sheath through which the opening and closing operating member and the adjusting wire are inserted and in which the forceps member is positioned at the distal end side thereof,
   wherein the adjusting member is provided at the distal end side of the sheath.

* * * * *